United States Patent [19]

Reynolds et al.

[11] 3,938,994
[45] Feb. 17, 1976

[54] PYRYLIUM DYES FOR ELECTROPHOTOGRAPHIC COMPOSITION AND ELEMENT

[75] Inventors: George A. Reynolds; James A. Van Allan; Lawrence E. Contois, all of Rochester, N.Y.

[73] Assignee: Eastman Kodak Company, Rochester, N.Y.

[22] Filed: June 18, 1974

[21] Appl. No.: 480,331

Related U.S. Application Data

[63] Continuation of Ser. No. 235,845, March 17, 1972.

[52] U.S. Cl.................................. 96/1.6; 260/345.1
[51] Int. Cl.²........................................ G03G 5/06
[58] Field of Search.............................. 96/1.6, 1.7

[56] References Cited
UNITED STATES PATENTS

| | | | |
|---|---|---|---|
| 3,250,615 | 5/1966 | Van Allan et al. | 96/1.7 |
| 3,526,502 | 9/1970 | Murakami et al. | 96/1.6 X |
| 3,577,235 | 5/1971 | Coltois | 96/1.6 |
| 3,617,268 | 11/1971 | Murakami et al. | 96/1.6 X |
| 3,694,462 | 9/1972 | Grisdale | 96/1.6 X |

*Primary Examiner*—Roland E. Martin, Jr.
*Attorney, Agent, or Firm*—R. P. Hilst

[57] ABSTRACT

This invention relates to organic compounds useful as sensitizers for organic photoconductive compositions having one of the following formulas:

I.

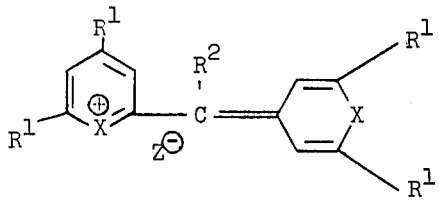

II.

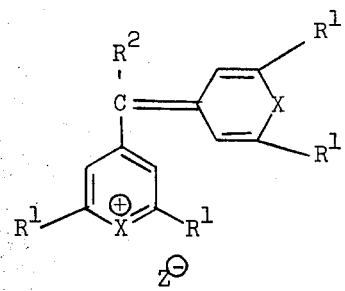

wherein:

$R^1$ represents a hydrogen atom, an alkyl radical having 1 to about 15 carbon atoms, a substituted alkyl radical wherein the alkyl moiety contains from 1 to about 15 carbon atoms and wherein the substituents are phenyl radicals or alkoxy radicals containing 1 to about 4 carbon atoms, a phenyl radical, and a substituted phenyl radical having as substituents alkyl radicals having 1 to about 15 carbon atoms or alkoxy radicals having 1 to about 4 carbon atoms;

$R^2$ represents $R^1$ and a radical having the following formula:

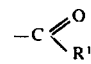

X represents a hetero atom selected from the group consisting of an oxygen and a sulfur atom; and $Z^-$ is an anionic function.

8 Claims, No Drawings

PYRYLIUM DYES FOR ELECTROPHOTOGRAPHIC COMPOSITION AND ELEMENT

This is a continuation of application Ser. No. 235,845, filed Mar. 17, 1972.

This invention relates to organic compounds useful as sensitizers in photoconductive compositions and electrophotographic elements.

The process of xerography, as disclosed by Carlson in U.S. Pat. No. 2,297,691, employs an electrophotographic element comprising a support material bearing a coating of a normally insulating material whose electrical resistance varies with the amount of incident actinic radiation it receives during an imagewise exposure. The element, commonly termed a photoconductive element, is first given a uniform surface charge after a suitable period of dark adaptation. The element is then exposed to a pattern of actinic radiation which has the effect of differentially reducing the potential of the surface charge in accordance with the relative energy contained in various parts of the radiation pattern. The differential surface charge or electrostatic latent image remaining on the electrophotographic element is then made visible by contacting the surface with a suitable electroscopic marking material. Such marking material or toner, whether contained in an insulating liquid or on a dry carrier, can be deposited on the exposed surface in accordance with either the charge pattern or in the absence of charge pattern as desired. The deposited marking material can then be either permanently fixed to the surface of the sensitive element by known means such as heat, pressure, solvent vapor and the like or transferred to a second element to which it may similarly be fixed. Likewise, the electrostatic latent image can be transferred to a second element and developed there.

Various photoconductive insulating materials have been employed in the manufacture of electrophotographic elements. For example, vapors of selenium and vapors of selenium alloys deposited on a suitable support and particles of photoconductive zinc oxide held in a resinous, film-forming binder have found wide application in present-day document copying applications.

Since the introduction of electrophotography, a great many organic compounds have been found to possess some degree of photoconductivity. Many organic compounds such as trinitrofluorenone have revealed a useful level of photoconduction and have been incorporated into photoconductive compositions. Optically clear organic photoconductor-containing elements having desirable electrophotographic properties can be especially useful in electrophotography. Such electrophotographic elements may be exposed through a transparent base, if desired, thereby providing unusual flexibility in equipment design. Such compositions when coated as a film or layer on a suitable support also yield an element which is reusable; that is, it can be used to form subsequent images after residual toner from prior images has been removed by transfer and/or cleaning.

Although many of the organic photoconductor materials are inherently light sensitive, their degree of sensitivity is usually low so that it is often necessary to add materials to increase their speed. Increasing the electrophotographic speed has several advantages in that it reduces exposure time, allows projection printing through various optical systems, etc. By increasing the speed through the use of sensitizers, photoconductors which would otherwise have been unsatisfactory are useful in processes where higher speeds are required. Accordingly, there is a need for new materials useful as sensitizers of organic photoconductor-containing systems.

Pyrylium salts, as disclosed in Davis et al, U.S. Pat. No. 3,141,770 issued July 21, 1964 and in VanAllan et al., U.S. Pat. No. 3,250,615 issued May 10, 1966, have been found to be useful sensitizing compounds for photoconductive compositions, especially organic photoconductive compositions. In addition, it has been found that certain individual species of pyrylium salts may advantageously be used in combination with various photoconductive compositions to provide improved sensitivity effects in particular regions of the spectrum such as the far red and near infrared region of the spectrum. See Contois et al., U.S. Pat. No. 3,586,500 issued June 22, 1971 and Contois U.S. Pat. No. 3,577,235 issued May 4, 1971. Other species of pyrylium salts have been found to be useful as sensitizers for low-color photoconductive compositions as disclosed in VanAllan, U.S. Pat. No. 3,554,745, issued Jan. 12, 1971. Other species of pyrylium salt sensitizers are disclosed in Defensive Publications T889,021; T889,022; and T889,023 all issued on Aug. 31, 1971. Still other species of pyrylium salt sensitizers are disclosed in Belgian Pat. No. 754,066 dated Sept. 30, 1970, and in Reynolds et al, U.S. Patent application Ser. No. 60,634 filed Aug. 3, 1970 and now abandoned.

One problem associated with certain of the above-noted pyrylium salt sensitizers is that many of these sensitizers do not impart sensitivity to organic photoconductive compositions in which they have been incorporated in that range of the visible spectrum extending from about 570 to about 620 millimicrons. Roughly, this corresponds to visible light appearing to the human eye as having a yellow hue. Thus, organic photoconductive compositions sensitized with certain of the above-noted sensitizers have sensitivity "holes" in the yellow region of the electromagnetic spectrum, i.e., such compositions have little or no sensitivity to yellow light.

In accordance with the present invention, it has been discovered that organic photoconductive compositions containing a sensitizing amount of certain pyrylium and thiapyrylium salts defined hereinafter do exhibit good spectral sensitivity in that portion of the visible spectrum extending from about 570 to about 620 millimicrons. Advantageously, it has been found that many of the sensitizers useful in the present invention also possess light-bleachability properties. Thus, background discoloration which may be imparted to an image-bearing electrophotographic element containing certain of the sensitizers of the present invention may easily be removed or at least substantially reduced by exposure of the element to light radiation. This property is especially advantageous where one wishes to obtain a good differential between the image-bearing and background areas of an electrophotographic element.

Typical of the sensitizing pyrylium and thiapyrylium salts of the present invention are compounds having the formulas represented below:

I.

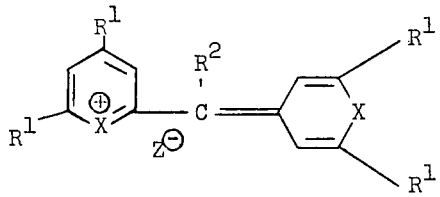

wherein

R[1] is a hydrogen atom; an alkyl radical having 1 to about 15 carbon atoms such as methyl, ethyl, isopropyl, butyl, t-butyl, amyl, isoamyl, hexyl, Z-ethylhexyl, octyl nonyl, decyl, dodecyl, and the like; substituted alkyl radicals wherein the alkyl moiety contains from 1 to about 15 carbon atoms and wherein the substituents are aryl radicals such as phenyl groups and exhibits alkoxy radicals containing 1 to about 4 carbon atoms including methoxy, ethoxy, propoxy, butoxy, etc.; an aryl radical such as phenyl; a substituted aryl radical having octyl, substituents alkyl radicals as described above and aliphatic alkoxy radicals containing 1 to about 4 carbon atoms as described above;

R[2] is R[1] and a radical having the formula

X is an oxygen or sulfur atom; and

Z[⊖] is an anionic function including such anions as perchlorate, tetrafluoroborate, p-toluenesulfonate, sulfonate, periodate, chloride, bromide, fluoride, iodide, sulfate, chloroaluminate, chloroferrate, etc.

II.

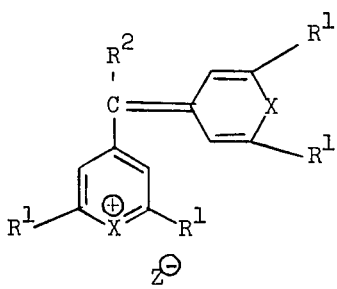

wherein R[1], R[2], X, and Z[⊖] are as defined above.

A highly useful class of sensitizer compounds according to the present invention are compounds having formulas I and II above and wherein X is an oxygen hetero atom.

Useful sensitizers according to this invention include the following representative compounds:
1. 2,4-Diphenyl-6-(2,6-diphenyl-4H-pyran-4-ylidenemethyl)-pyrylium perchlorate
2. 2,6-Diphenyl-4-(2,6-diphenyl-4H-pyran-4-ylidenemethyl)-pyrylium perchlorate
3. 4-(Benzoyl-2,6-diphenyl-4H-pyran-4-ylidenemethyl)2,6-diphenylpyrylium perchlorate
4. 2,6-Bis(4-amyloxyphenyl)-4-[2-(4-amyloxyphenyl)-6-phenyl-4H-pyran-4-ylidenemethyl]-pyrylium perchlorate Generally, the sensitizing activity of the pyrylium and thiapyrylium salts of this invention is not affected by the type of anionic function employed. The selection of suitable anions is influenced, however, by several factors including: (1) ease of synthesis and isolability of the salt; (2) stability of the salt; (3) compatibility of the salt with the system in which it is incorporated; (4) solubility of the salt; etc. The anions of the pyrylium and thiapyrylium salts of this invention can be interchanged as desired by simple metathesis with an anion of another acid.

Electrophotographic elements can be prepared with a variety of organic photoconductive compounds and the sensitizing compounds of this invention in the usual manner, i.e., by blending a dispersion or solution of the photoconductive compound together with an electrically insulating, film-forming resin binder when necessary or desirable and coating or forming a self-supporting layer with the photoconductive composition. Generally, a suitable amount of the sensitizing compound is mixed with the photoconductive coating composition so that after thorough mixing, the sensitizing compound is uniformly distributed throughout the desired layer of the coated element. The amount of sensitizer that can be added to a photoconductor-containing layer to give effective increases in speed can vary widely. The optimum concentration in any given case will vary with the specific photoconductor and sensitizing compound used.

In general, an appropriate sensitizer is added in a concentration range from about 0.0001 to about 30 percent by weight based on the weight of the film-forming coating composition. Normally, the sensitizer is added to the coating composition in an amount from about 0.005 to about 10 percent by weight of the total coating composition.

The sensitizers used in this invention are effective for enhancing the electrophotosensitivity of a wide variety of photoconductors. Photoconductors useful in sensitive compositions containing the present sensitizers are described below.

1. Arylamine photoconductors including substituted and unsubstituted arylamines, diarylamines, nonpolymeric triarylamines and polymeric triarylamines such as those described in Fox U.S. Pat. No. 3,240,597, issued Mar. 15, 1966 and Klupfel et al., U.S. Pat. No. 3,180,730, issued Apr. 27, 1965;

2. Polyarylalkane photoconductors of the types described in Noe et al. U.S. Pat. No. 3,274,000, issued Sept. 20, 1966, Wilson U.S. Pat. No. 3,542,547, issued Nov. 24, 1970 and in Seus et al. U.S. Pat. No. 3,542,544, issued Nov. 24, 1970;

3. 4-Diarylamino-substituted chalcones of the types described in Fox U.S. Pat. No. 3,526,501, issued Sept. 1, 1970;

4. Non-ionic cycloheptenyl compounds of the types described in Looker U.S. Pat. No. 3,533,786, issued Oct. 13, 1970;

5. Compounds containing an

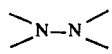

nucleus, as described in Fox U.S. Pat. No. 3,542,546, issued Nov. 24, 1970;

6. Organic compounds having a 3,3'-bis-aryl-2-pyrazoline nucleus, as described in Fox et al. U.S. Pat. No. 3,527,602, issued Sept. 8, 1970;

7. Triarylamines in which at least one of the aryl radicals is substituted by either a vinyl radical or a vinylene radical having at least one active hydrogen-containing group, as described in Brantly et al. U.S. Pat. No. 3,567,450, issued Mar. 2, 1971;

8. Triarylamines in which at least one of the aryl radicals is substituted by an active hydrogen-containing group, as described in Brantly et al. Belgian Pat. No. 728,563, dated Apr. 30, 1969;

9. Any other organic compound which exhibits photoconductive properties such as those set forth in Australian Pat. No. 248,402 and the various polymeric photoconductors such as the photoconductive carbazol polymers described in U.S. Pat. No. 3,421,891, dated Jan. 14, 1969.

Preferred binders for use in preparing the photoconductive layers which can be sensitized in accordance with the method of this invention comprise polymers having fairly high dielectric strength which are good electrically insulating film-forming vehicles. Materials of this type comprise styrene-butadiene copolymers; silicone resins; styrene-alkyd resins; silicone alkyd resins; soya-alkyd resins; poly(vinyl chloride); poly(vinylidene chloride); vinylidene chloride-acrylonitrile copolymers; poly(vinyl acetate); vinyl acetate-vinyl chloride copolymers; poly(vinyl acetals), such as poly(vinyl butyral); polyacrylic and methacrylic esters, such as poly(methylmethacrylate), poly(n-butylmethacrylate), poly(isobutyl methacrylate), etc; polystyrene; nitrated polystyrene; polymethylstyrene; isobutylene polymers; polyesters, such as poly(ethylene alkaryloxyalkylene terephthalate); phenol-formaldehyde resins; ketoneresins; polyamides; polycarbonates; polythiocarbonates; poly(ethyleneglycol-co-bishydroxyethoxyphenylpropane terephthalate); nuclear substituted polyvinyl haloarylates; etc. Methods of making resins of this type have been described in the prior art, for example, styrene-alkyd resins can be prepared according to the method described in U.S. Pat. Nos. 2,361,019 and 2,258,423. Suitable resins of the type contemplated for use in the photo-conductive layers of the invention are sold under such trademarks as Vitel PE-101, Cymac, Piccopale 100, Saran F-220 and Lexan 105 and 145. Other types of binders which can be used in the photoconductive layers of the invention include such materials as paraffin, mineral waxes, etc. If a polymeric photoconductor is used, the binder may be omitted altogether.

The organic coating solvents useful for preparing the above coating dopes can be selected from a variety of materials. Useful liquids are hydrocarbon solvents, including substituted hydrocarbon solvents, with preferred materials being halogenated hydrocarbon solvents. The requisite properties of the solvent are that it be capable of dissolving the pyrylium dye and capable of dissolving or at least highly swelling or solubilizing the polymeric ingredient of the composition. In addition, it is helpful if the solvent is volatile, preferably having a boiling point of less than about 200°C. Particularly useful solvents include halogenated lower alkanes having from 1 to about 3 carbon atoms, such as dichloromethane, dichloroethane, dichloropropane, trichloromethane, trichloroethane, tribromomethane, trichloromonofluoromethane, trichlorotrifluoroethane, etc.; aromatic hydrocarbons such as benzene, toluene as well as halogenated benzene compounds such as chlorobenzene, bromobenzene, dichlorobenzene, etc.; ketones such as dialkyl ketones having 1 to about 3 carbon atoms in the alkyl moiety such as dimethylketone, methylethylketone, etc.; and ethers such as tetrahydrofuran, etc. Mixtures of these and other solvents can also be used.

In preparing the photoconductive coating composition, useful results are obtained where the photoconductor substance is present in an amount equal to at least about 1 weight percent of the coating composition. The upper limit in the amount of photoconductor substance present can be widely varied in accordance with usual practice. In those cases where a binder is employed, it is normally required that the photoconductor substance be present in an amount from about 1 weight percent of the coating composition to about 99 weight percent of the coating composition. A polymeric photoconductor can be employed in which case an additional binder may not be required. A preferred weight range for the photoconductor substance in the coating composition is from about 10 weight percent to about 60 weight percent.

Suitable supporting materials for coating photoconductive layers which can be sensitized in accordance with the method of this invention can include any of a wide variety of electrically conducting supports, for example, paper (at a relative humidity above 20 percent); aluminum-paper laminates; metal foils such as aluminum foil, zinc foil, etc; metal plates, such as aluminum, copper, zinc, brass and galvanized plates; vapor deposited metal layers such as silver, nickel, aluminum and the like coated on paper or conventional photographic film bases such as cellulose acetate, polystyrene, etc. Such conducting materials as nickel can be vacuum deposited on transparent film supports in sufficiently thin layers to allow electrophotographic elements prepared therewith to be exposed from either side of such elements. An especially useful conducting support can be prepared by coating a support material such as poly(ethylene terephthalate) with a conducting layer containing a semiconductor dispersed in a resin. Such conducting layers both with and without insulating barrier layers are described in U.S. Pat. No. 3,245,833. Likewise, a suitable conducting coating can be prepared from the sodium salt of a carboxyester lactone of maleic anhydride and a vinyl acetate polymer. Such kinds of conducting layers and methods for their optimum preparation and use are disclosed in U.S. Pat. No. 3,007,901 and 3,262,807.

Coating thicknesses of the photoconductive composition on the support can vary widely. Normally, a coating in the range of about 10 microns to about 300 microns before drying is useful for the practice of this invention. The preferred range of coating thickness is found to be in the range from about 50 microns to about 150 microns before drying, although useful results can be obtained outside of this range. The resultant dry thickness of the coating is preferably between about 2 microns and about 50 microns, although useful results can be obtained with a dry coating thickness between about 1 and about 200 microns.

The elements of the present invention can be employed in any of the well-known electrophotographic processes which require photoconductive layers. One such process is the xerographic process. In a process of this type, an electrophotographic element is held in the dark and given a blanket electrostatic charge by placing it under a corona discharge. This uniform charge is retained by the layer because of the substantial dark insulating property of the layer, i.e., the low conductivity of the layer in the dark. The electrostatic charge formed on the surface of the photoconductive layer is then selectively dissipated from the surface of the layer by image-wise exposure to light by means of a conventional exposure operation such as, for example, by a contact-printing technique, or by lens projection of an image, and the like, to thereby form a latent electrostatic image in the photoconductive layer. Exposing the surface in this manner forms a pattern of electrostatic charge by virtue of the fact that light energy striking the photoconductor causes the electrostatic charge in the light struck areas to be conducted away from the surface in proportion to the intensity of the illumination in a particular area.

The charge pattern produced by exposure is then developed or transferred to another surface and developed there, i.e., either the charged or uncharged areas rendered visible, by treatment with a medium comprising electrostatically responsive particles having optical density. The developing electrostatically responsive particles can be in the form of a dust, i.e., powder, or a pigment in a resinous carrier, i.e., toner. A preferred method of applying such toner to a latent electrostatic image for solid area development is by the use of a magnetic brush. Methods of forming and using a magnetic brush toner applicator are described in the following U.S. Pat. Nos.: Young U.S. Pat. No. 2,786,439 issued Mar. 26, 1957; Giaimo U.S. Pat. No. 2,786,440 issued Mar. 26, 1957; Young U.S. Pat. No. 2,786,441 issued Mar. 26, 1957; Greig U.S. Pat. No. 2,874,063 issued Feb. 17, 1959. Liquid development of the latent electrostatic image may also be used. In liquid development, the developing particles are carried to the image-bearing surface in an electrically insulating liquid carrier. Methods of development of this type are widely known and have been described in the patent literature, for example, Metcalfe et al. U.S. Pat. No. 2,907,674 issued Oct. 6, 1959. In dry developing processes, the most widely used method of obtaining a permanent record is achieved by selecting a developing particle which has as one of its components a low-melting resin. Heating the powder image then causes the resin to melt or fuse into or on the element. The powder is, therefore, caused to adhere permanently to the surface of the photoconductive layer. In other cases, a transfer of the electrostatic charge image formed on the photoconductive layer can be made to a second support such as paper which would then become the final print after development and fusing. Techniques of the type indicated are well known in the art and have been described in the literature in "RCA Review" Vol. 15 (1954) pages 469–484.

The following examples are included for a further understanding of the invention.

EXAMPLE 1

Preparation of
2,6-Diphenyl-4-(2,6-diphenyl-4H-pyron-4-ylidenemethyl)-pyrylium perchlorate A mixture of 1.24 g. of 2,6-diphenyl-4-pyrone, 1.73 g. of 2,6-diphenyl-4-methylpyrylium perchlorate and 20 ml. of acetic anhydride is heated to reflux for 20 min. The dark mixture is cooled and the green dye which separates is collected. The product is recrystallized by extraction with acetonitrile in a Soxhlet extractor to yield a sample having a melting point of 325°C. The theoretical calculated values for $C_{35}H_{25}ClO_6$ and the actual values found are as follows:

Cal'd.: C=72.8; H=4.3; Cl=6.2.
Found: C=72.4; H=4.6; Cl=6.0.

In an alternative method for preparing the above compound, 3.6 g. of 2,6-diphenyl-4-methoxypyrylium perchlorate and 1.5 g. of malonic acid are added to 100 ml. of ethanol. After also adding 3 ml. of ethyldiisopropylamine, the mixture is heated on a steam bath. After about 10 minutes heating, the red reaction mixture is cooled slightly and made strongly acid with $HClO_4$. The red color changes to brown and a solid separates. The solid is collected, washed with ethanol, and recrystallized from acetonitrile to yield a product having a m.p. of 330°C.

EXAMPLE 2

Preparation of
2,4-Diphenyl-6-(2,6-diphenyl-4H-pyran-4-ylidenemethyl)pyrylium perchlorate A mixture of 3.5 g. of 2,4-diphenyl-6-methylpyrylium perchlorate, 2.5 g. of 2,6-diphenyl-4-pyrone and 40 ml. of acetic anhydride is refluxed for 15 minutes, cooled, and the solid is collected, washed with ether, and recrystallized from acetic anhydride. A product having a m.p. of 258° C. is obtained. The theoretical values for $C_{35}H_{25}ClO_6$ and the actual values are as follows:

Cal'd.: C=72.8; H=4.4; Cl=6.1.
Found: C=72.5; H=4.5; Cl=6.1.

EXAMPLE 3

Preparation of
4-(Benzoyl-2,6-diphenyl-4H-pyran-4-ylidenemethyl)-2,6-diphenylpyrylium perchlorate A mixture of 5.0 g. of 2,6-diphenyl-4-pyrone and 4.8 ml. of acetophenone in 10 ml. of $POCL_3$ is heated on a steam bath for 15 minutes. The reaction mixture is cooled, poured slowly into methanol, and then 5 ml. of $HOIO_4$ is added slowly with stirring. The reaction mixture is allowed to cool and the nicely formed crystals are collected. The product is recrystallized by extraction with acetonitrile in a Soxhlet extractor. A product having a melting point of 271°C. is obtained. The theoretical values calculated for $C_{42}H_{29}ClO_7$ and the actual values found are as follows:

Cal'd.: C=74.0; H=4.3; Cl=5.2.
Found : C=73.6; H=4.0; Cl=5.5.

EXAMPLE 4

Preparation of
2,6-Bis(4-amyloxyphenyl)-4-[2-(4-amyloxyphenyl)-6-phenyl-4H-pyran-4-ylidenemethyl]pyrylium perchlorate:

A mixture of 3.1 g. of 2,6-bis(4-amyloxyphenyl)-4-methylpyrylium perchlorate, 2.0 g. of 2-(4-amyloxyphenyl)-6-phenyl-4-pyrone, and 20 ml. of acetic anhydride are stirred and heated at its boiling temperature for 5 to 10 minutes, cooled, diluted with ethanol with stirring, and chilled in a freezer. A solid separates from the mixture and is collected and washed with water. Another crop is obtained by adding water to the reaction mixture, extracting with dichloromethane, removing the solvent by evaporation, and recrystallizing the residue from acetic acid. The two crops are combined and recrystallized again from acetic acid, mp = 68°C. The theoretical values calculated for $C_{50}H_{55}ClO$, and the actual values found are as follows:

Cal'd.: C=71.9; H=6.6; Cl=4.2. Found: C=71.7; H=6.7; Cl=4.0.

EXAMPLE 5

General Procedure for the Preparation of Pyranylidene-methylthiapyrylium Salts

A solution of 2 g. of sodium sulfide in 10 ml. of water is added to 2 g. of the pyranomethylenepyrylium salt in 50 ml. of acetone. The mixture is stirred for 0.5 hour, then made strongly acidic with dilute perchloric acid, and stirred for an additional hour. The solid is collected, washed with water and crystallized.

Using this procedure 2,6-Diphenyl-4-[(2,6-diphenyl-4H-pyran-4-ylidene)methyl]thiapyrylium perchlorate is obtained in 75% yield and melts at 270°–271°C. after recrystallization from acetonitrile. The λmax (acetonitrile) ($\epsilon \times 10^{-3}$) are 238(33.5), 257(31.7), 390(21.6), ~555, and 585 mμ (80.1).

The theoretical calculated values for $C_{35}H_{25}ClO_5S$ and the values actually found are as follows:

Cal'd: C=70.9; H=4.3; S=5.4. Found: C=70.9; H=4.2; S=5.4.

Using the above-described general procedure 4,6-Diphenyl-2-[(2,6-diphenyl-4H-pyran-4-ylidene)methyl]thiapyrylium perchlorate is obtained in 36% yield and melts at 302°–303°C. after crystallization from acetonitrile.

The theoretical calculated values for $C_{35}H_{25}ClO_5S$ and the actual values found are as follows:

Cal'd.: C=70.9; H=4.3; S=5.4. Found: C=70.8; H=4.6; S=5.4.

EXAMPLE 6

A series of photoconductive compositions containing one of the following photoconductors:
A. triphenylamine
B. 4,4'-bis(diethylamino)-2,2'-dimethyltriphenyl methane
C. 4,4'-bis(diphenylaminochalcone)

as the photoconductive material are prepared for coating on a conducting support material by mixing 0.25 parts of the photoconductor with 0.01 parts by weight of one of the following compounds:
1.  2,4-Diphenyl-6-(2,6-diphenyl-4H-pyran-4-ylidenemethyl)-pyrylium perchlorate
2.  2,6-Diphenyl-4-(2,6-diphenyl-4H-pyran-4-ylidenemethyl)-pyrylium perchlorate
3.  4-(Benzoyl-2,6-diphenyl-4H-pyran-4-ylidenemethyl)2,6-diphenyl-pyrylium perchlorate
4.  2,6-Bis(4-amyloxyphenyl)-4-[2-(4-amyloxyphenyl)-6-phenyl-4H-pyran-4-ylidenemethyl]pyrylium perchlorate as sensitizer and dissolving the mixture, together with 1.0 parts by weight of a resinous polyester binder, by stirring the mix into dichloromethane. The resultant mixture is then hand coated over a polymeric carboxy ester lactone layer carried on a transparent support. In all instances, the polyester binder in the coating composition is Vitel PE-101 (trademark of Goodyear Tire and Rubber Co.) and is believed to be poly(4,4'-isopropylidene-bisphenoxy ethyl-co-ethylene terephthalate) 50/50. The wet coating thickness on the support is 0.004 inch. After drying, a sample of each electrophotographic element is employed in a standard xerographic process which includes charging under a positive corona discharge until the surface potential of the sample, as measured by an electrometer probe, reaches 600 volts. Similarly, a sample of each element is charged under a negative source until the surface potential reaches 600 volts. Each of the samples is then exposed from behind a transparent stepped density gray scale to a 3000°K tungsten source of 20 foot-candle illuminance at the point of exposure. The exposure causes reduction of surface potential of the element under each step of the gray scale from its initial potential, Vo, to some lower potential, V, the exact value of which depends upon the actual amount of exposure received by each area. The results of these measurements are then plotted on a graph of surface potential V versus log exposure for each step. The actual speed of each element can then be expressed in terms of the reciprocal of the exposure required to reduce the surface potential to any fixed arbitrarily assigned value. Numerically, the shoulder speeds noted below are the quotient of $10^4$ divided by the exposure in meter candle seconds required to reduce the potential by 100 volts. The toe speeds noted below are the quotient of $10^4$ divided by the exposure in meter-candle-seconds required to reduce the initial voltage, Vo, to an absolute value of 100 volts. The results of these speed measurements are given in the following table.

TABLE I

| Compound Number | Organic Photoconductor | Positive Shoulder | Positive Toe | Negative Shoulder | Negative Toe |
|---|---|---|---|---|---|
| 1 | A | 1700 | 150 | 4000 | 100 |
|   | B | 1500 | 120 | 1700 | 100 |
|   | C | 2200 | 200 | 1800 | 100 |
| 2 | A | 1800 | 110 | 1400 | 85 |
|   | B | 1600 | 100 | 900 | 63 |
|   | C | 1800 | 160 | 1100 | 80 |
| 3 | A | 1500 | 110 | 2500 | 56 |
|   | B | 1000 | 71 | 800 | 35 |
|   | C | 2500 | 290 | 900 | 63 |
| 4 | A | 900 | 36 | 800 | 31 |
|   | B | 1400 | 78 | 1000 | 59 |
|   | C | 1100 | 80 | 630 | 40 |

For comparison, photoconductors A, B and C employed in the photoconductive compositions used to obtain the data shown in Table I are evaluated in samples containing no sensitizer. The speeds are as follows:

| Organic Photoconductor | Positive Shoulder | Positive Toe | Negative Shoulder | Negative Toe |
|---|---|---|---|---|
| A | 44 | 0 | 52 | 0 |
| B | 19 | 0 | 18 | 0 |
| C | 101 | 0 | 32 | 0 |

The invention has been described in detail with particular reference to preferred embodiments thereof, but, it will be understood that variations and modifications can be effected within the spirit and scope of the invention.

We claim:
1. A photoconductive composition comprising an organic photoconductive electrically insulating material containing a sensitizing amount of a compound selected from the group consisting of:

1. 2,4-Diphenyl-6-(2,6-diphenyl-4H-pyran-4-ylidenemethyl)-pyrylium salts
2. 2,6-Diphenyl-4-(2,6-diphenyl-4H-pyran-4-ylidenemethyl)-pyrylium salts
3. 4-(Benzoyl-2,6-diphenyl-4H-pyran-4-ylidenemethyl)2,6-diphenyl-pyrylium salts and
4. 2,6-Bis(4-amyloxyphenyl)-4-[2-(4-amyloxyphenyl)-6-phenyl-4H-pyran-4-ylidenemethyl]-pyrylium salts, said composition exhibiting photoconductive sensitivity to visible light in that portion of the spectrum extending from about 570 to about 620 millimicrons.

2. A photoconductive composition as defined in claim 1 wherein the sensitizer is selected from the group consisting of:
1. 2,4-Diphenyl-6-(2,6-diphenyl-4H-pyran-4-ylidenemethyl)-pyrylium perchlorate
2. 2,6-Diphenyl-4-(2,6-diphenyl-4H-pyran-4-ylidenemethyl)-pyrylium perchlorate
3. 4-(Benzoyl-2,6-diphenyl-4H-pyran-4-ylidenemethyl)2,6-diphenyl-pyrylium perchlorate
4. 2,6-Bis(4-amyloxyphenyl)-4-[2-(4-amyloxyphenyl)-6-phenyl-4H-pyran-4-ylidenemethyl]-pyrylium perchlorate.

3. A photoconductive composition as described in claim 1 wherein the photoconductive electrically insulating material comprises a mixture of an organic photoconductor and an electrically insulating, film-forming resin binder.

4. A photoconductive composition as in claim 3 wherein the organic photoconductor is selected from the group consisting of an arylamine, a polyarylalkane and a diarylamino-substituted chalcone.

5. An electrophotographic element comprising a support having coated thereon a layer of a photoconductive composition as described in claim 1.

6. An element as in claim 5 wherein the photoconductive electrically insulating material comprises a mixture of an organic photoconductor and an electrically insulating, film-forming resin binder.

7. An electrophotographic element as in claim 6 wherein the organic photoconductor is selected from the group consisting of an arylamine, a polyarylalkane and a diarylaminosubstituted chalcone.

8. An electrophotographic element as in claim 5 wherein the support is electrically conducting.

* * * * *